United States Patent
Nathanson

(10) Patent No.: US 7,544,174 B2
(45) Date of Patent: Jun. 9, 2009

(54) QUIET FLEXION/EXTENSION STOP FOR ORTHOPEDIC BRACE AND ORTHOPEDIC BRACE INCORPORATING A QUIET FLEXION/EXTENSION STOP

(75) Inventor: Jeremy Nathanson, San Clemente, CA (US)

(73) Assignee: DJO, LLC, Vista, CA (US)

(*) Notice: Subject to any disclaimer, the term of this patent is extended or adjusted under 35 U.S.C. 154(b) by 59 days.

(21) Appl. No.: 11/540,925

(22) Filed: Sep. 29, 2006

(65) Prior Publication Data

US 2008/0082031 A1    Apr. 3, 2008

(51) Int. Cl.
*A61F 5/00*    (2006.01)
(52) U.S. Cl. .................. 602/16; 602/26; 602/27
(58) Field of Classification Search .......... 602/16, 602/20, 23, 26, 27; 128/882, 892; 623/27, 623/57
See application file for complete search history.

(56) References Cited

U.S. PATENT DOCUMENTS

| | | | |
|---|---|---|---|
| 401,933 A | 4/1889 | DeCamp | |
| 2,883,982 A | 4/1959 | Rainey | |
| 3,473,527 A | 10/1969 | Spiro | |
| 4,366,813 A | 1/1983 | Nelson | |
| 4,370,977 A | 2/1983 | Mauldin et al. | |
| 4,732,143 A | 3/1988 | Kausek et al. | |
| 4,817,588 A | 4/1989 | Bledsoe | |
| 4,838,251 A | 6/1989 | Chignon et al. | |
| 4,865,024 A | 9/1989 | Hensley et al. | |
| 5,038,765 A * | 8/1991 | Young et al. | 602/16 |
| 5,261,871 A | 11/1993 | Greenfield | |
| 5,358,469 A | 10/1994 | Patchel et al. | |
| 5,419,754 A | 5/1995 | Hutchins | |
| 5,437,611 A | 8/1995 | Stern | |
| 5,437,619 A | 8/1995 | Malewicz et al. | |
| 5,443,444 A | 8/1995 | Pruyssers | |
| 5,472,412 A | 12/1995 | Knoth | |
| 5,632,725 A * | 5/1997 | Silver et al. | 602/26 |
| 5,658,241 A | 8/1997 | Deharde et al. | |
| 5,662,596 A | 9/1997 | Young | |
| 5,676,640 A | 10/1997 | Biedermann | |
| 5,749,840 A | 5/1998 | Mitchell et al. | |
| 5,873,847 A | 2/1999 | Bennett et al. | |
| 5,954,677 A | 9/1999 | Albrecht et al. | |
| 5,980,435 A | 11/1999 | Joutras et al. | |
| 6,004,283 A | 12/1999 | Young | |
| 6,074,355 A * | 6/2000 | Bartlett | 602/16 |
| 6,129,690 A | 10/2000 | Hamlin et al. | |
| RE37,209 E | 6/2001 | Hensley et al. | |
| 6,387,066 B1 | 5/2002 | Whiteside | |
| 6,402,711 B1 | 6/2002 | Nauert | |

(Continued)

FOREIGN PATENT DOCUMENTS

EP    0 262 758    4/1988

(Continued)

*Primary Examiner*—Michael A. Brown
(74) *Attorney, Agent, or Firm*—Ropes & Gray LLP

(57) ABSTRACT

The present flexion and/or extension stop includes a body portion constructed of a hard and durable material and at least one bumper portion constructed of a soft and resilient material. The stop provides quiet operation and non-jarring motion termination for the wearer. The stop also provides positive range of motion control, strength and durability. Also disclosed is an orthopedic brace incorporating the present flexion and/or extension stop.

13 Claims, 7 Drawing Sheets

U.S. PATENT DOCUMENTS

| | | |
|---|---|---|
| 6,666,837 B2 | 12/2003 | Weihermüller |
| 6,752,775 B2 | 6/2004 | Seligman et al. |
| 2004/0049140 A1 | 3/2004 | Doty et al. |
| 2004/0153015 A1 | 8/2004 | Seligman et al. |

FOREIGN PATENT DOCUMENTS

| | | |
|---|---|---|
| WO | WO 86/04228 | 6/2001 |

* cited by examiner

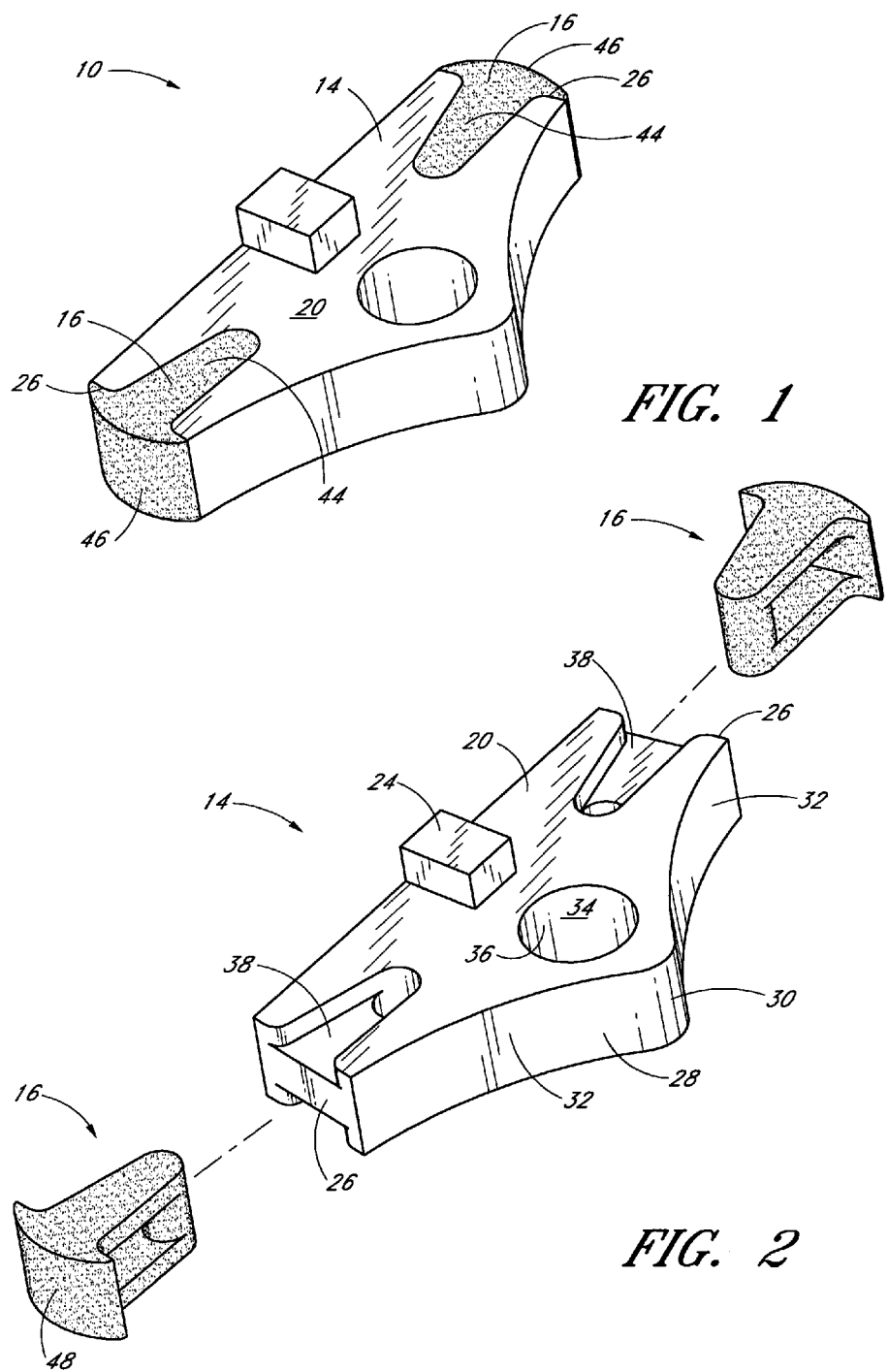

QUIET FLEXION/EXTENSION STOP FOR ORTHOPEDIC BRACE AND ORTHOPEDIC BRACE INCORPORATING A QUIET FLEXION/EXTENSION STOP

BACKGROUND OF THE INVENTION

1. Field of the Invention

The present invention relates to orthopedic bracing, and more specifically to apparatus and methods for decelerating an orthosis to prevent hyperextension and/or hyperflexion.

2. Description of the Related Art

Many orthopedic braces are configured to be secured to an extremity of a wearer to control the motion of a joint. For example, one common category of braces is configured to be secured to the wearer's leg in order to support the knee. Such braces may be used in a post-operative setting, or to prevent injury to a healthy knee, for example. Many of these knee braces include one or more mechanisms that control the range of motion of the knee and prevent the wearer from hyperextending and/or hyperflexing the knee.

A mechanical stop is one common mechanism for controlling the range of knee motion. Such a stop is positioned within the hinge and in the plane of rotation of the hinge arm(s) to thereby interfere with the hinge motion at one or more prescribed angular settings. When the hinge arm(s) reaches the prescribed angular setting, it (they) contacts the stop and the stop prevents the hinge arm(s) from rotating any farther. The hinge may include an extension stop to limit the range of motion as the knee is extended, or a flexion stop to limit the range of motion as the knee is flexed. The hinge may also include both an extension stop and a flexion stop.

Mechanical stops are generally constructed of hard materials, because they must be capable of withstanding high stresses. For example, metals like steel, zinc, or aluminum are frequently used. Similar materials are also generally used to construct the hinge arms, which must also be capable of withstanding high stresses. Unfortunately, as a metal hinge arm contacts a metal stop, an audible clicking sound is often made. This noise can be an annoyance to brace wearers. Further, as metal contacts metal, motion of the brace comes to an abrupt halt, which can be jarring and uncomfortable for brace wearers.

Some mechanical stops are constructed of relatively soft and flexible materials. Soft stops can reduce noise within a brace and increase wearer comfort by dampening the impact between a hinge arm and the stop. However, the qualities of soft stops that make them attractive for reducing noise and increasing wearer comfort also make them less attractive for achieving other objectives. For example, soft stops are generally not durable enough to withstand the high stresses that can be applied to mechanical stops. Further, the flexibility of a soft stop reduces the capability of the stop to provide precise motion control. If it is desired to prevent a knee brace wearer from flexing his or her knee past a certain angle, a soft stop may disadvantageously flex too much, thus allowing the wearer's knee to flex past the desired angle.

SUMMARY OF THE INVENTION

The preferred embodiments of the present quiet flexion/extension stop for orthopedic brace have several features, no single one of which is solely responsible for their desirable attributes. Without limiting the scope of this quiet flexion/extension stop as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include quiet operation, the capability to bring the orthopedic brace to a gradual halt instead of an abrupt halt, and the capability to withstand high stresses.

One aspect of the present quiet flexion/extension stop for orthopedic brace includes the realization that wearers of orthopedic braces would benefit from a flexion/extension stop that produces very little, if any, audible noise when impacted by a component of the brace, such as a hinge arm. Another aspect of the present stop includes the realization that wearers of orthopedic braces would benefit from a flexion/extension stop that brings brace motion to a gradual halt instead of an abrupt halt. Another aspect of the present stop includes the realization that mechanical stops are preferably able to withstand high stresses, but that materials that are able to withstand such stresses are generally not practical for producing a stop that makes little noise. Therefore, it would be beneficial to combine harder and more durable materials with softer and quieter materials.

One embodiment of the present quiet flexion/extension stop is configured for use with an orthopedic brace. The stop comprises a body portion constructed of a relatively hard and rigid material. The stop further comprises at least one bumper portion cooperating with and being supported by the body portion. The bumper portion is constructed of a relatively soft and resilient material.

Another embodiment of the present quiet flexion/extension stop comprises a method of absorbing energy during an impact in an orthopedic brace. The method comprises the step of applying the orthopedic brace to an extremity of a wearer. The orthopedic brace includes at least one hinge arm and at least one flexion and/or extension stop. The method further comprises the step of flexing or extending the extremity, thereby imparting kinetic energy to the hinge arm, and continuing to flex or extend the extremity until the hinge arm contacts the stop. When the hinge arm contacts the stop a resilient bumper portion of the stop deforms, thereby absorbing at least a first portion of the kinetic energy of the hinge arm. At least a second portion of the kinetic energy of the hinge arm is transmitted through the resilient bumper portion and absorbed by a rigid body portion of the stop.

BRIEF DESCRIPTION OF THE DRAWINGS

The preferred embodiments of the present quiet flexion/extension stop for orthopedic brace, illustrating its features, will now be discussed in detail. These embodiments depict the novel and non-obvious flexion/extension stop shown in the accompanying drawings, which are for illustrative purposes only. These drawings include the following figures, in which like numerals indicate like parts:

FIG. 1 is a top perspective view of one embodiment of the present quiet flexion/extension stop for orthopedic brace;

FIG. 2 is a top perspective view of the quiet flexion/extension stop of FIG. 1, illustrating the elastomeric bumpers exploded from the rigid body;

DETAILED DESCRIPTION OF THE PREFERRED EMBODIMENTS

FIG. 1 illustrates one embodiment of the present quiet flexion/extension stop 10 for an orthopedic brace. As those of ordinary skill in the art will readily appreciate, the present stop 10 is configured for use in any orthopedic brace. For example, the stop 10 may be employed within a knee brace 12 (FIG. 8), an elbow brace (not shown) or any other brace. For simplicity, the stop 10 will be described herein with reference to a knee brace. This description, however, should not be interpreted as limiting the range of applications for the present stop 10, or as limiting the scope of protection for the current stop 10, as defined by the claims below.

The stop 10 is configured for use as either a flexion stop or an extension stop, depending upon where it is positioned with respect to hinge arms of the brace. For example, in a knee brace the stop 10 would function as an extension stop if it were positioned anteriorly of the hinge arms, and as a flexion stop if it were positioned posteriorly of the hinge arms.

Figure 3:
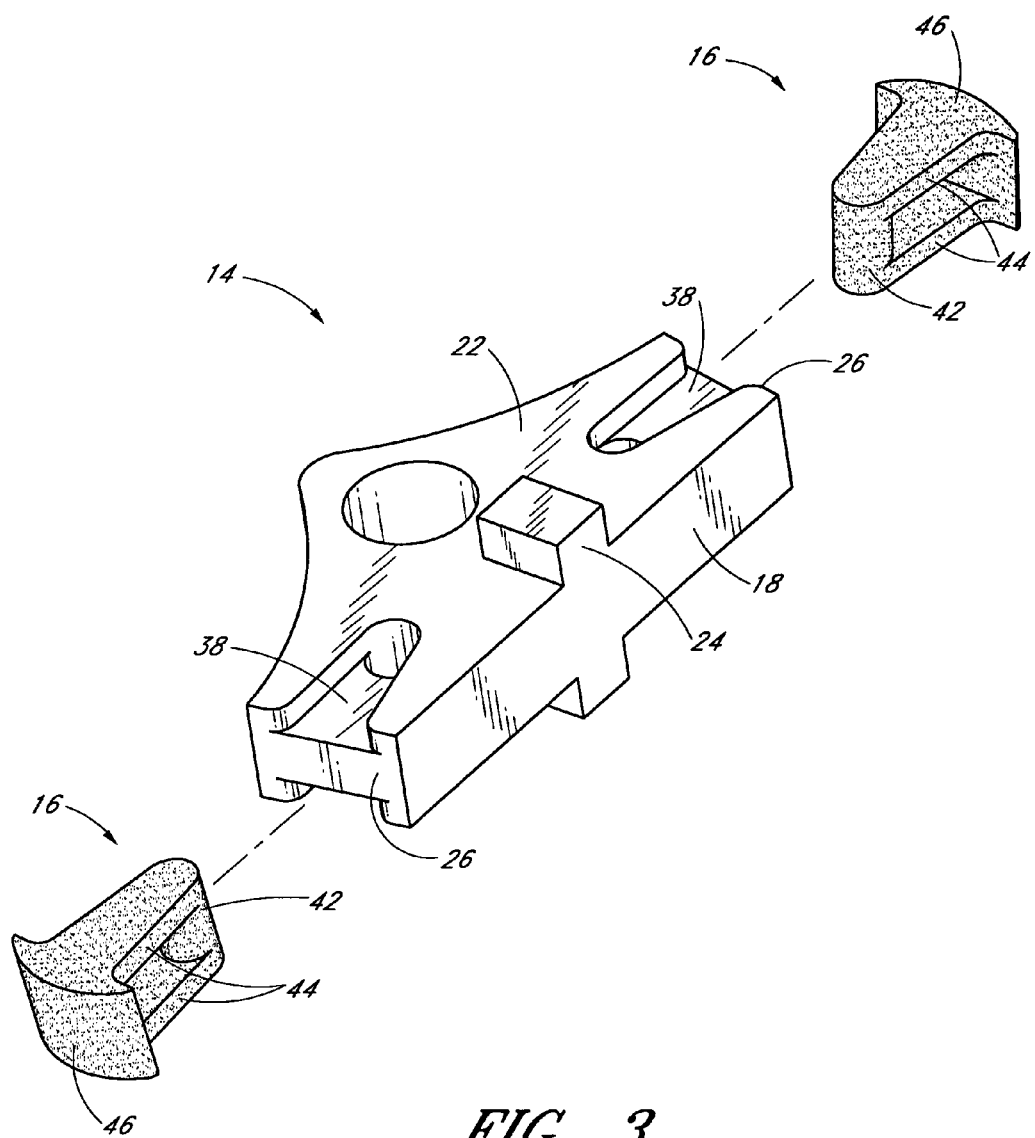
FIG. 3 is a bottom perspective view of the quiet flexion/extension stop of FIG. 2.

With reference to FIGS. 1-3, the stop 10 includes a body portion 14 that is constructed of a hard, rigid and durable material capable of withstanding relatively high stresses. For example, the body portion 14 may be constructed of a metal, such as iron, steel, zinc, nickel, beryllium, titanium, aluminum, magnesium or any alloys of these metals. The body portion 14 may also be constructed of a ceramic, a polymer or any other material having the desired properties described above.

The stop 10 further comprises first and second bumper portions 16. The bumper portions 16 are constructed of a material that is relatively soft, flexible and resilient. The material may be elastomeric. Examples of materials that may be used to construct the bumper portions 16 include natural or synthetic rubber, thermoplastic elastomer, plastic, SANTOPRENE®, urethane, silicone, neoprene, nylon, polyethylene and polypropylene. The bumper portions 16 are positioned at opposite ends of the body portion 14, and are configured to absorb impacts. While the illustrated embodiment includes two bumper portions 16, those of ordinary skill in the art will appreciate that the present stop 10 could include only one bumper portion, or more than two bumper portions.

Those of ordinary skill in the art will appreciate that the present stop 10 could have virtually any shape, and could be virtually any size. The illustrated embodiments are merely examples. With reference to FIGS. 2 and 3, the body portion 14 includes a substantially flat rear surface 18 and substantially flat top 20 and bottom 22 surfaces. When describing the stop 10 in isolation, all directional terms used herein have been arbitrarily assigned, without regard to a brace in which the stop 10 might be used, and without regard to how the stop 10 might be oriented relative to a brace wearer.

Each of the top and bottom surfaces 20, 22 includes a protrusion 24 shaped substantially as a rectangular parallelepiped. The protrusions 24 extend in opposite directions from the stop 10, and are located adjacent the rear surface 18 and substantially midway between the ends 26 of the stop 10. The protrusions 24 are adapted to engage mating portions in a hinge plate or hinge plates (not shown). Those of ordinary skill in the art will appreciate that the protrusions 24 could be any shape and/or size. Those of ordinary skill in the art will further appreciate that the protrusions 24 need not be provided at all. The stop 10 could be secured to a hinge plate another way, such as with one or more screws.

Figure 4:
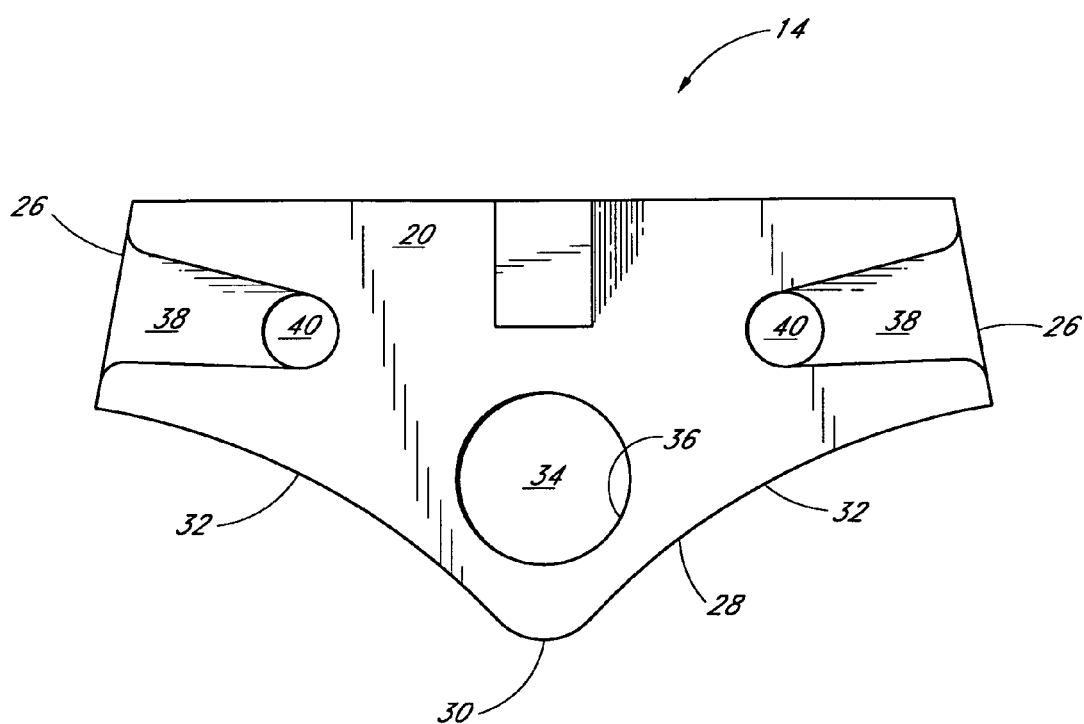
FIG. 4 is a top plan view of the rigid body of the quiet flexion/extension stop of FIG. 2.

With reference to FIGS. 2 and 4, a front surface 28 of the body portion 14 includes a rounded peak 30 substantially midway between the ends 26 of the stop 10, with first and second radiused portions 32 sloping away from the peak 30. A through-hole 34 extends from the top surface 20 to the bottom surface 22 of the stop 10. In the illustrated embodiment, the through-hole 34 has a substantially round cross-section and a smooth inner wall surface 36. However, those of ordinary skill in the art will appreciate that the through-hole 34 could have virtually any cross-sectional shape, and need not have a smooth inner wall surface 36. For example, the inner wall surface 36 could be threaded.

The through-hole 34 is configured to receive a fastening member, such as a screw, that may secure the stop 10 to a hinge plate (not shown). However, those of ordinary skill in the art will appreciate that the through-hole 34 need not be provided. The stop 10 could be secured to a hinge plate in a variety of other ways, such as with an adhesive.

With reference to FIGS. 2 and 4, the top surface 20 of the body portion 14 includes first and second recesses 38 located at opposite ends 26 of the body portion 14. In the illustrated embodiment, the recesses 38 are substantially U-shaped when viewed from above (FIG. 4), open in opposite directions, and extend to the ends 26 of the body portion 14. Identically shaped and oriented recesses 38 are located on the bottom surface 22 of the body portion 14, as illustrated in FIG. 3. Those of ordinary skill in the art will appreciate that the recesses 38 could have any shape and/or depth. At the base of each recess 38, an aperture 40 extends through the body portion 14 and connects each recess 38 on the top surface 20 to its counterpart on the bottom surface 22.

With reference to FIGS. 2 and 3, each bumper portion 16 is sized and shaped to fill the aperture 40 and recesses 38 at either end 26 of the body portion 14, with an additional portion of the bumper extending outward from the body portion end 26. Accordingly, and with reference to FIG. 3, each bumper portion 16 includes a substantially cylindrical anchor portion 42 that is received within one of the apertures 40 in the body portion 14. Those of ordinary skill in the art will appreciate that the shape of the anchor portion 42 may be determined by the shape of the aperture 40 in which it is received. Therefore, if the apertures 40 are shaped differently than as shown, the anchor portions 42 may also have different shapes.

First and second connecting portions 44 extend from upper and lower ends of the anchor portion 42. The connecting portions 44 are shaped to fill the recesses 38, with each connecting portion 44 lying flush with a respective one of the top and bottom surfaces 20, 22 of the body portion 14 (FIG. 1). Opposite the anchor portion 42, ends of each connecting portion 44 adjoin a head portion 46. The head portion 46 protrudes from the end 26 of the body portion 14 (FIG. 1) and includes a rounded end surface 48 (FIG. 2). Each head portion 46 forms a rounded shock absorber at the ends 26 of the body portion 14.

In one embodiment, the stop 10 of FIGS. 1-3 is constructed by molding the bumper portions 16 around the body portion 14. First, the body portion 14 is placed into a mold cavity. Then, a liquefied form of the bumper portion material is injected into the mold cavity. The bumper portions 16 solidify around the body portion 14, with the bumper portion material filling the recesses 38 and apertures 40 in the body portion 14, and extending beyond the ends 26 of the body portion 14 to form the rounded head portions 46. Those of ordinary skill in the art will appreciate that the stop 10 could be manufactured through alternative processes, and that the process just described is merely one example.

In the injection molding process just described, the injected material advantageously flows into and fills the apertures 40 and the recesses 38 in the body portion 14, thereby creating the anchor portion 42 and the connecting portions 44. The rounded head portions 46 form as the injected material fills the voids in the mold cavity at either end 26 of the body portion 14. The one-piece bumper portions 16 form a mechanical interlock between the body portion 14 and the bumper portions 16. This configuration prevents disassembly of the stop 10 in the event that the injected material does not adhere to or chemically bond with the body portion 14. However, those of ordinary skill in the art will appreciate that the bumper portions 16 could be configured differently. Each bumper portion 16 could, for example, be constructed of multiple pieces. Those of ordinary skill in the art will also appreciate that within an assembled hinge one or more hinge plates and/or bearing plates (not shown) may abut the top and/or bottom surfaces 20, 22 of the stop 10. The plate(s) may similarly abut the connecting portions 44 of the bumper portions 16 to secure the bumper portions 16 to the body portion 14.

Figure 5:
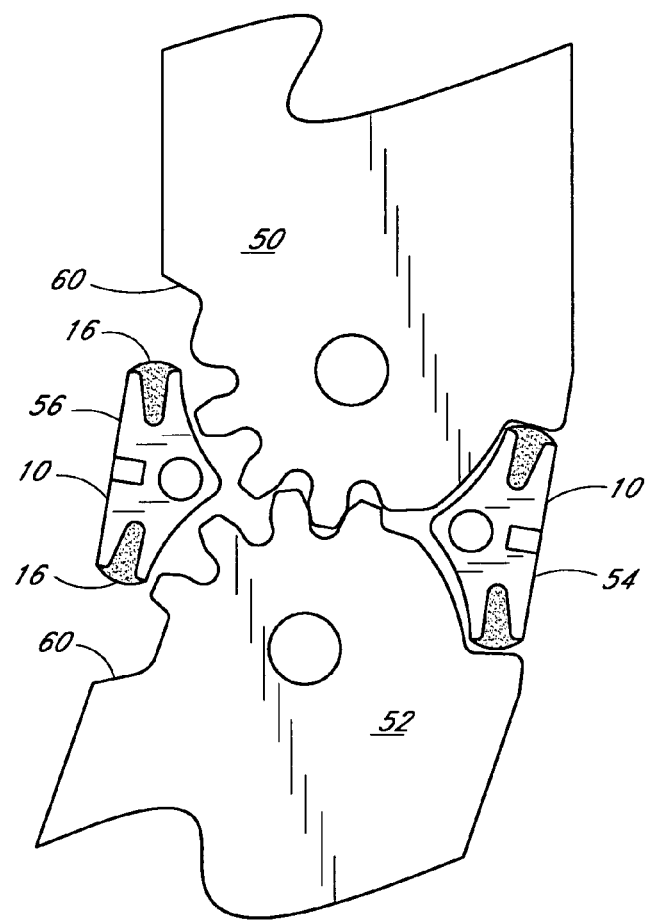
FIG. 5 is a schematic top plan view of first and second hinge arms of an orthopedic brace, a flexion stop identical to the quiet flexion/extension stop of FIG. 1 and an extension stop identical to the quiet flexion/extension stop of FIG. 1, illustrating the hinge arms near full extension.
Figure 6:
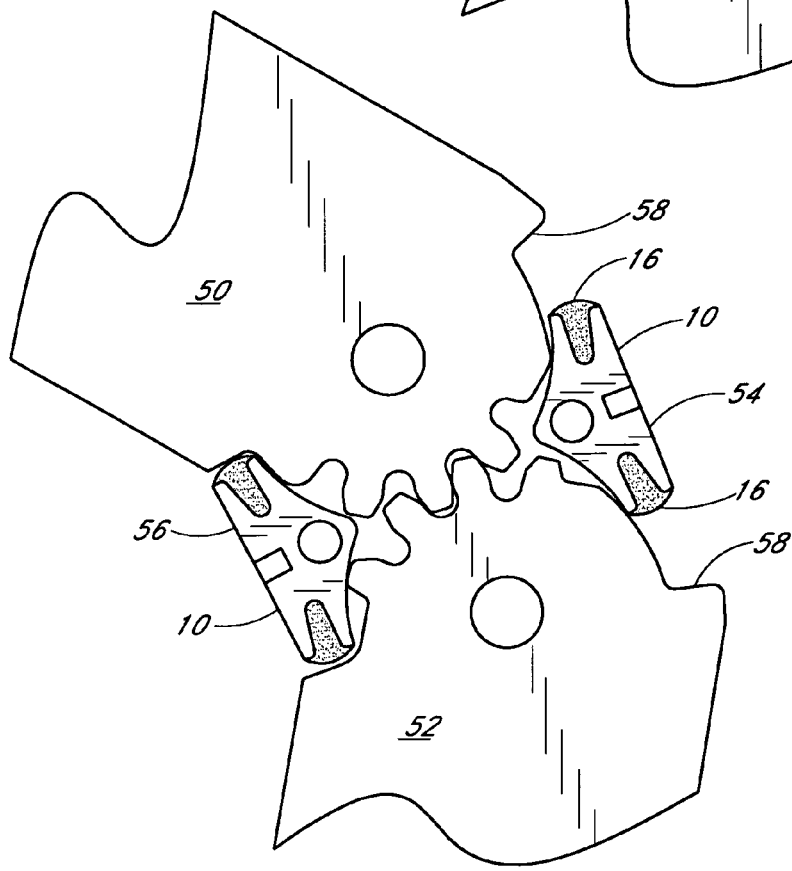
FIG. 6 is a schematic top plan view of the components of FIG. 5, illustrating the hinge arms near full flexion.
Figure 8:
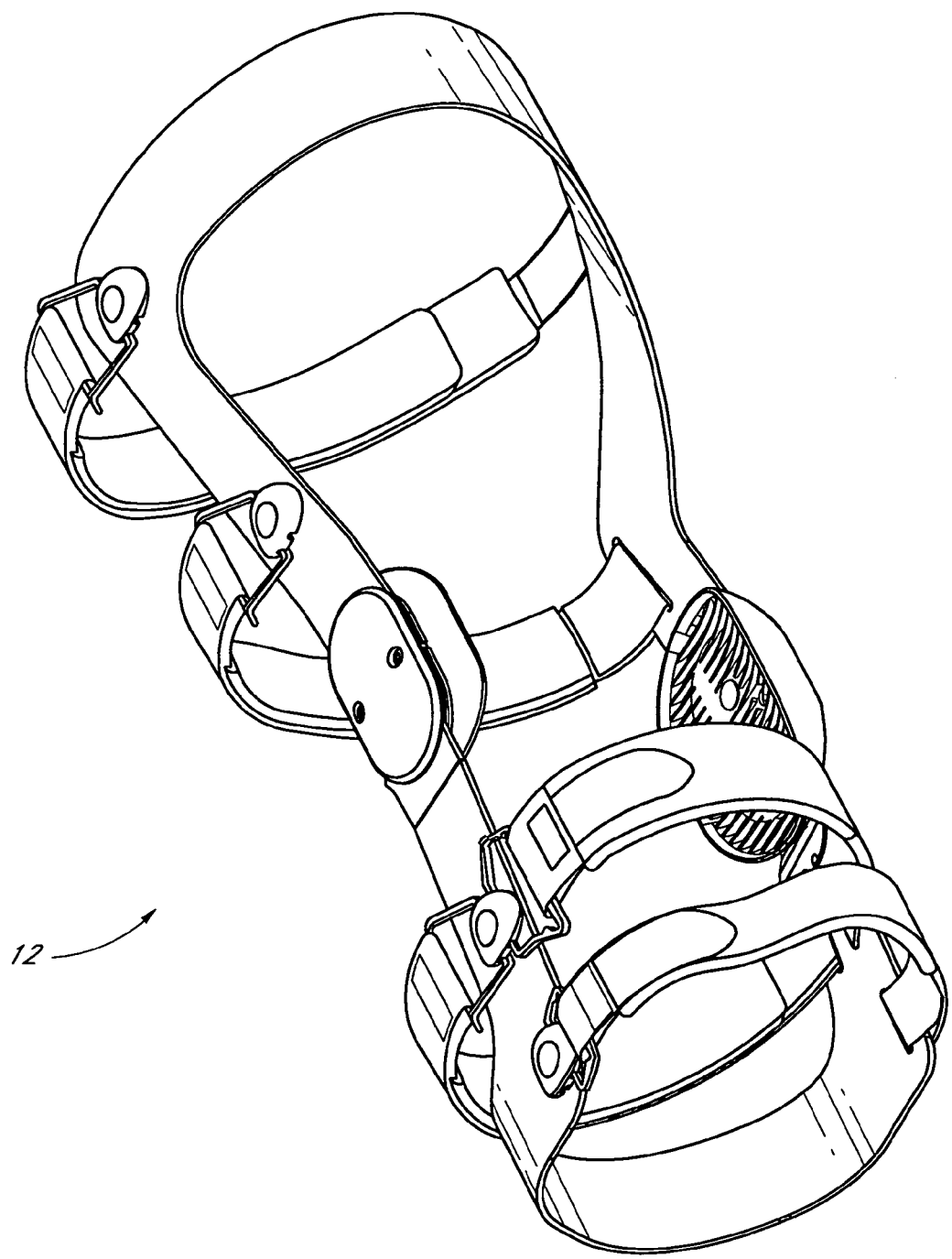
FIG. 8 is a front perspective view of an orthopedic knee brace including the present flexion/extension stop.

The present stop 10 is configured to be readily incorporated into an orthopedic brace, such as the knee brace 12 illustrated in FIG. 8. With reference to FIGS. 5 and 6, in one embodiment the stop 10 may be located in the plane of rotation of a first hinge arm 50 and a second hinge arm 52. A first stop 10 is located anteriorly of the hinge arms 50, 52 to serve as an extension stop 54. A second stop 10 is located posteriorly of the hinge arms 50, 52 to serve as a flexion stop 56. However, those of ordinary skill in the art will appreciate that in certain embodiments only one stop 10 may be provided, and the stop 10 may serve as either an extension stop 54 or a flexion stop 56. Those of ordinary skill in the art will also appreciate in certain embodiments only one hinge arm may be provided.

The hinge arm(s) 50, 52 and the stop(s) 10 may all be secured to one or more hinge plates (not shown). For example, the through-hole 34 in each stop 10 may receive a fastening member, such as a screw, that secures the stop 10 to the hinge plate. The protrusions 24 on the top and bottom faces of the stop 10 may also engage features of the hinge plate to further secure the stop 10 to the hinge plate.

As shown in FIGS. 5 and 6, each hinge arm includes an anterior shoulder 58 and a posterior shoulder 60. With reference to FIG. 5, the extension stop 54 is positioned and oriented so that as a flexion angle of the hinge arms 50, 52 decreases, when a desired flexion angle is reached the anterior shoulders 58 contact the bumpers 16 at the ends of the extension stop 54. With reference to FIG. 6, the flexion stop 56 is positioned and oriented so that as a flexion angle of the hinge arms 50, 52 increases, when a desired flexion angle is reached the posterior shoulders 60 contact the bumpers 16 at the ends of the flexion stop 56. The curved head portions 48 of the bumpers 16 deform to absorb the force of the impacts from the shoulders 58, 60. After impact, the hinge arms 50, 52 decelerate to a full stop as the shoulders 58, 60 squeeze the resilient bumper material. The harder material of the body portion 14 supports the relatively soft bumpers 16, ensuring that the hinge arms 50, 52 will come to a halt at the desired flexion angle. The flexible and resilient bumpers 16, however, bring the hinge arms 50, 52 to a more gradual halt as compared to a stop that is constructed of only a relatively hard material. The bumpers 16 thus prevent the type of jarring halt that can occur in a knee brace that does not include bumpers. The bumpers 16 also produce relatively little noise as compared to stops that are made from only relatively hard materials. Each of these benefits can make it more likely that a given brace wearer will comply with a prescribed treatment program.

The present quiet flexion/extension stop 10 presents a number of advantages over prior art designs. For example, fully elastomeric stops tend to lack strength and durability. They also can deform so severely as to provide very limited range of motion (ROM) control, and can deform to the point of cracking or failing under high strain levels. To increase the strength, durability and functionality of a fully elastomeric stop, one is forced to use harder materials. As harder and harder materials are used, the stop tends to generate more and more noise, and to provide increasingly jarring halts to joint motion.

In the embodiments of the present stops 10, flexible and resilient bumper portions 16 are supported and reinforced by a harder and stronger body portion 14. This design provides a stop 10 that is strong, functional and durable, and yet provides quiet and smooth deceleration to joint motion. This design provides these benefits while maintaining ROM control. By backing the resilient bumpers with harder supporting materials, the amount of strain that the bumpers experience can be controlled to increase the lifespan of the stop 10.

Figure 7:
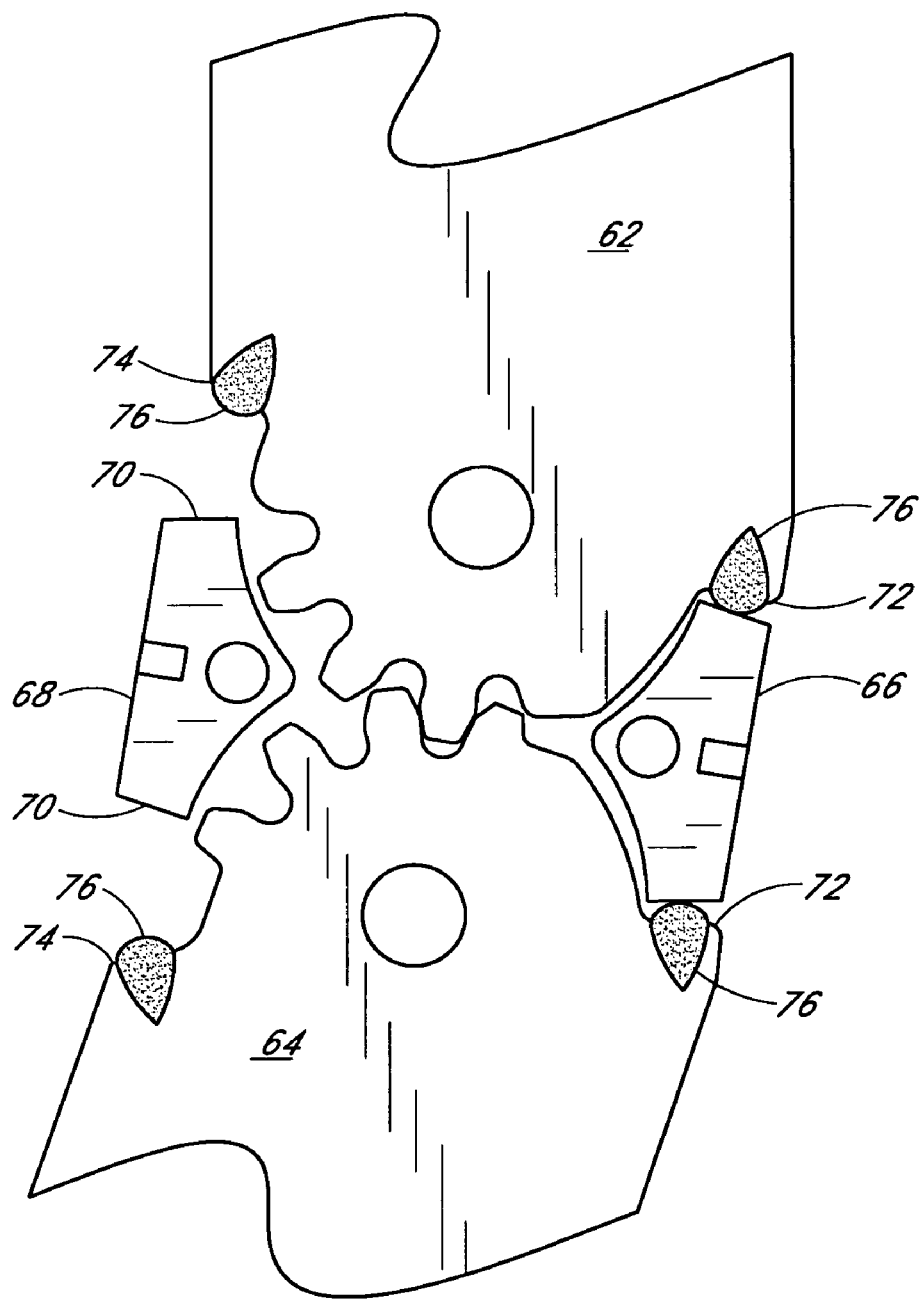
FIG. 7 is a schematic top plan view of first and second hinge arms of an orthopedic brace, a flexion stop and an extension stop, illustrating the hinge arms near full extension and including elastomeric bumpers cooperating with the hinge arms.

FIG. 7 illustrates an alternative embodiment of the present stops, wherein soft and resilient material is provided on hinge arms 62, 64. The apparatus of FIG. 7 includes an extension stop 66 and a flexion stop 68. Each stop 66, 68 is constructed of a hard and durable material, such as the materials described above with respect to the body portion 14. The shape and configuration of each stop 66, 68 is similar to the stop 10 described above, except that the recesses 38 and apertures 40 are absent. Each stop 66, 68 includes substantially flat ends 70.

Each hinge arm 62, 64 includes an anterior shoulder 72 and a posterior shoulder 74. Each shoulder 72, 74 includes a bumper portion 76 that is constructed of soft and resilient material, such as the materials described above with respect to the bumper portions 16. Each bumper portion 76 is similar in shape and configuration to the bumper portions 16 described above. The bumper portions 76 may be constructed in a similar manner to that described above, wherein the hinge arms 62, 64 are placed in a mold and the bumper material is injected to fill apertures and recesses (not shown) in the hinge arms 62, 64.

The operation of the apparatus shown in FIG. 7 is similar to the apparatus shown in the previous figures and described above. Therefore, the operation and benefits of this apparatus will not be described in detail. The apparatus of FIG. 7 is essentially the same as that illustrated in FIGS. 5 and 6, except that the soft and resilient material has been transferred from the stops to the hinge arms. The hinge arms 62, 64 and bumper portions 76 provide quiet operation and non-jarring motion termination while at the same time providing a durable construction that is capable of withstanding high stresses.

Figure 9:
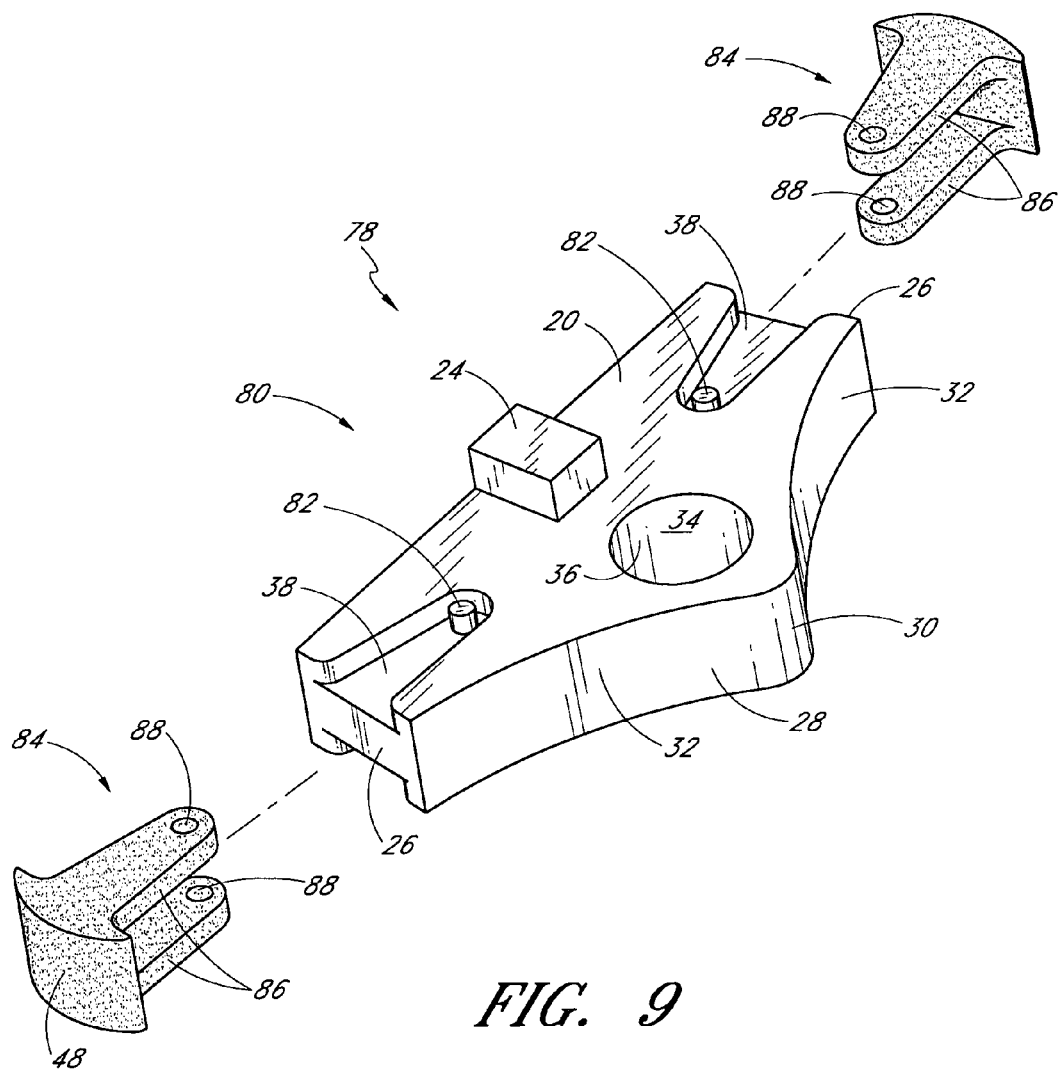
FIG. 9 is a top perspective view of another embodiment of the present quiet flexion/extension stop for orthopedic brace.

FIG. 9 illustrates an alternative embodiment of the present flexion/extension stop. The stop 78 includes a body portion 80 that is substantially similar to the body portion 14 described above. However, the body portion 80 of FIG. 9 does not include the apertures 40 that are shown in FIGS. 2-4. Instead, each recess 38 includes a post 82 extending out of the recess 38 and located near a base of the recess 38. Although not shown in FIG. 9, counterpart posts may be provided on the bottom side of the body portion 80.

The stop 78 also includes first and second bumper portions 84 that are substantially similar to the bumper portions 16 described above. However, the bumper portions 84 of FIG. 9 do not include the anchor portions 42 that are shown in FIGS. 2 and 3. Instead, each connecting portion 86 includes an aperture 88 that is positioned to mate with one of the posts 82 on the body portion 80. The interlocking of the posts 82 and the apertures 88 secures the bumper portions 84 to-the body portion 80. One or more hinge plates and/or bearing plates (not shown) may also overlie the top and bottom surfaces of the stop 78 to further secure the bumper portions 84 to the body portion 80, as described above with respect to the stop 10.

In one embodiment, the stop 78 of FIG. 9 may be constructed using an injection molding process, similar to the process described above with respect to the stop 10. In the stop 78, however, the bumper portions 84 do not interlock with the body portion 78 in the same way that the bumper portions 16 interlock with the body portion 14 in the stop 10. Rather, the bumper portions 84 may be removed from the body portion 78 by bending the connecting portions 86 out of the recesses 38 so as to disengage the posts 82 from the apertures 88. The bumper portions 84 may then be pulled away from the body portion 78. The removability of the bumper portions 84 facilitates replacement of worn bumper portions 84. The removability of the bumper portions 84 also facilitates exchanging one bumper portion 84 with another that might have a different hardness, size, shape, etc. A brace wearer can thus tailor the behavior of his or her brace to different activities, or provide different performance characteristics in conformance with a therapy schedule.

SCOPE OF THE INVENTION

The above presents a description of the best mode contemplated for carrying out the present quiet flexion/extension stop for orthopedic brace, and of the manner and process of making and using it, in such full, clear, concise, and exact terms as to enable any person skilled in the art to which it pertains to make and use this flexion/extension stop. This flexion/extension stop is, however, susceptible to modifications and alternate constructions from that discussed above that are fully equivalent. Consequently, this flexion/extension stop is not limited to the particular embodiments disclosed. On the contrary, this flexion/extension stop covers all modifications and alternate constructions coming within the spirit and scope of the flexion/extension stop as generally expressed by the following claims, which particularly point out and distinctly claim the subject matter of the flexion/extension stop.

What is claimed is:

1. A flexion and/or extension stop configured for use with an orthopedic brace, the stop comprising:
   a body portion, the body portion being constructed of a relatively hard and rigid material;
   at least one bumper portion associated with the body portion, the bumper portion being constructed of a relatively soft and resilient material;
   wherein the bumper portion associated with the bofy portion configured to secure the bumper portion to the body portion; and
   wherein the anchor portion comprises a substantially cylindrical aperture that is received by a post in the body portion.

2. The flexion and/or extension stop of claim 1, wherein the at least one bumper portion cooperates with and is supported by the body portion.

3. The flexion and/or extension stop of claim 1, wherein the at least one bumper portion is constructed of an elastomeric material.

4. The flexion and/or extension stop of claim 1, wherein the bumper portion includes a protruding head portion.

5. The flexion and/or extension stop of claim 4, wherein the protruding head portion includes a curved end surface.

6. The flexion and/or extension stop of claim 4, wherein at least one connecting element connects the protruding head portion to the anchor portion.

7. The flexion and/or extension stop of claim 6, further comprising a second connecting element that connects the protruding end portion and the anchor portion to one another.

8. The flexion and/or extension stop of claim 1, wherein the body portion includes at least one feature configured to cooperate with an anchor portion of the bumper portion to secure the bumper portion to the body portion.

9. The flexion and/or extension stop of claim 1, wherein the body portion at least one recessed portion configured to receive a connecting element of the bumper potion.

10. The flexion and/or extension of claim 1, further comprising a second bumper portion, and wherein the first bumper portion is located at first end of the body portion and the second bumper portion is located at a second end of the body portion opposite the first end.

11. The flexion and/or extension stop of claim 10, wherein each bumper portion includes a curved end surface, and the curved end surfaces face in substantially opposite directions.

12. An orthepedic brace including the flexion and /or extension stop of claim 1.

13. The orthopedic brace of claim 12, wherein the brace is a knee brace.

* * * * *

UNITED STATES PATENT AND TRADEMARK OFFICE
CERTIFICATE OF CORRECTION

PATENT NO. : 7,544,174 B2  Page 1 of 1
APPLICATION NO. : 11/540925
DATED : June 9, 2009
INVENTOR(S) : Jeremy Nathanson It is certified that error appears in the above-identified patent and that said Letters Patent is hereby corrected as shown below:

In the Claims:

In claim 1, column 8, line 9, please replace "associated with the bofy" with --includes an anchor--;

In claim 9, column 8, line 36, please replace "portion at least" with --portion includes at least--;

In claim 9, column 8, line 37, please replace "potion" with --portion--;

In claim 10, column 8, line 38, please replace "extension of claim 1" with --extension stop of claim 1--;

In claim 10, column 8, line 40, please replace "located at first" with --located at a first--; and In claim 12, column 8, line 46, please replace "orthepedic" with --orthopedic--.

Signed and Sealed this

Fourth Day of August, 2009

JOHN DOLL
*Acting Director of the United States Patent and Trademark Office*